United States Patent
Kusuda et al.

(10) Patent No.: US 9,850,551 B2
(45) Date of Patent: Dec. 26, 2017

(54) SACCHARIFIED SOLUTION PRODUCTION METHOD AND SACCHARIFIED SOLUTION PRODUCTION APPARATUS THAT USE CELLULOSIC BIOMASS AS STARTING MATERIAL

(71) Applicant: KAWASAKI JUKOGYO KABUSHIKI KAISHA, Kobe-shi, Hyogo (JP)

(72) Inventors: Hiromasa Kusuda, Kobe (JP); Noriaki Izumi, Kobe (JP); Hironori Tajiri, Kobe (JP); Shoji Tsujita, Itami (JP); Noriyuki Taniyama, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 290 days.

(21) Appl. No.: 14/655,485

(22) PCT Filed: Dec. 25, 2012

(86) PCT No.: PCT/JP2012/008270
§ 371 (c)(1),
(2) Date: Jun. 25, 2015

(87) PCT Pub. No.: WO2014/102858
PCT Pub. Date: Jul. 3, 2014

(65) Prior Publication Data
US 2015/0329926 A1  Nov. 19, 2015

(51) Int. Cl.
C13K 1/04 (2006.01)
C13K 1/02 (2006.01)
C12P 7/10 (2006.01)

(52) U.S. Cl.
CPC ..... *C13K 1/04* (2013.01); *C12P 7/10* (2013.01); *C13K 1/02* (2013.01); *Y02E 50/16* (2013.01); *Y02P 20/544* (2015.11)

(58) Field of Classification Search
CPC .... C13K 1/04; C13K 1/02; C12P 7/10; Y02E 50/16; Y02P 20/544
See application file for complete search history.

(56) References Cited

FOREIGN PATENT DOCUMENTS

| CN | 101972018 A | 2/2011 |
|----|-------------|--------|
| JP | S57-61624 A | 4/1982 |

(Continued)

OTHER PUBLICATIONS

Translation of the Written Opinion of the International Searching Authority for PCT/JP2012/008270, dated Apr. 2013.*

(Continued)

*Primary Examiner* — David A Reifsnyder
(74) *Attorney, Agent, or Firm* — Oliff PLC

(57) ABSTRACT

A saccharified solution production method includes: a saccharifying step of saccharifying hemicellulose or cellulose contained in cellulosic biomass to C5 or C6 saccharides by subjecting a slurry of cellulosic biomass to a hot water treatment in a supercritical state or subcritical state; a washing step of successively washing a solid in the slurry with washing water after the saccharifying step, by using multiple stages of thickeners for washing arranged in series so that the direction of movement of the solid in the slurry and the direction of movement of overflow water are opposite to each other; and a concentration step of removing a solid residue from the washing water recovered in the washing step by using a thickener for still standing that is different from the thickeners for washing, and then concentrating a supernatant of the thickener for still standing by using a concentration device to give a saccharified solution.

5 Claims, 4 Drawing Sheets

(56) References Cited

FOREIGN PATENT DOCUMENTS

| JP | H05-229816 A | 9/1993 |
| JP | 2010-081855 A | 4/2010 |
| JP | 2010-253348 A | 11/2010 |
| WO | 2012/042840 A1 | 4/2012 |

OTHER PUBLICATIONS

Jul. 11, 2016 Office Action issued in Chinese Patent Application No. 201280077782.8.
Apr. 16, 2013 Search Report issued in International Patent Application No. PCT/JP2012/008270.
Zhenhong Yuan et al., "Principles and Technologies of Bioenergy" Chemical Industry Press, First Edition, pp. 273-274, (2005).
Zhixin Jiang et al., "Hydrometallurgical Separation Engineering", Atomic Press, First Edition, pp. 165-166, (1993).

* cited by examiner

SACCHARIFIED SOLUTION PRODUCTION METHOD AND SACCHARIFIED SOLUTION PRODUCTION APPARATUS THAT USE CELLULOSIC BIOMASS AS STARTING MATERIAL

TECHNICAL FIELD

The present invention relates to a method for producing saccharides by hydrolyzing cellulosic biomass in a supercritical state or a subcritical state, and an apparatus used for such a method.

BACKGROUND ART

As part of biomass energy utilization, attempts are made to obtain ethanol by decomposition of cellulose or hemicellulose which is a principal component of plants. In such attempts, there are planned to use the obtained ethanol for fuel by partly mixing it mainly in automotive fuel or by using it as an alternative fuel for gasoline.

Principal components of plants include cellulose (polymer of glucose which is C6 monosaccharide composed of six carbons), hemicellulose (polymer of C5 monosaccharide composed of five carbons and C6 monosaccharide), lignin, and starch, and ethanol is generated by fermentation action of microorganisms such as yeast from saccharides such as C5 monosaccharide, C6 monosaccharide and oligosaccharide which is a complex of the monosaccharides.

For decomposition of cellulosic biomass such as cellulose or hemicellulose, the following three methods are planned to be industrially applied: 1) method of hydrolyzing by means of the oxidizing power of strong acid such as sulfuric acid, 2) method of enzymatically decomposing, and 3) method of utilizing the oxidizing power of supercritical water or subcritical water. However, in the acid decomposition method of 1), the added acid is an inhibitory substance for fermentation of yeast, and hence it is necessary to conduct a treatment of neutralizing the added acid before alcohol fermentation of saccharides after decomposition of cellulose or hemicellulose into saccharides, and this leads to difficulty in practical application for the economical reason in terms of the treatment cost. The enzymatic decomposition method 2) allows a treatment at a normal temperature and a constant pressure, however, an effective enzyme has not been found, and even if an effective enzyme is found, the production cost of the enzyme is probably high, and the prospects for industrial scale realization are still far from certain in the economical aspect.

As the method of hydrolyzing cellulosic biomass by supercritical water or subcritical water to produce saccharides of 3), Patent document 1 discloses a production method of saccharides capable of separating saccharides containing C5 monosaccharide and C6 monosaccharide from saccharides containing C6 monosaccharide and recovering them, in addition to obtaining saccharides from wood biomass with high yield and high efficiency. The production method of saccharides of Patent document 1 includes: a first slurry heating step (S1) of heating a slurry prepared by adding high-temperature, high-pressure water to wood biomass; a first separating step (S2) of separating the heated slurry into a liquid ingredient and a solid ingredient; a second slurry heating step (S3) of adding water to the separated solid ingredient to render it a slurry, and heating the slurry; a second separating step (S4) of separating the heated slurry into a liquid ingredient and a solid ingredient; and a useful ingredient acquiring step (S5) of removing water from the separated liquid ingredient to acquire saccharides; and is characterized by further acquiring saccharides by removing water from the liquid ingredient separated in the first separating step (S2) in addition to acquiring saccharides in the useful ingredient acquiring step (S5).

Patent document 2 discloses a method of hydrolyzing biomass that hydrolyzes biomass by the use of pressurized hot water, comprising: a first step of hydrolyzing mainly hemicellulose in the biomass; and a second step of hydrolyzing mainly cellulose in a residue obtained in the first step, wherein a liquid used in the first step includes a filtrate obtained by solid-liquid separation conducted after end of the second step. Patent document 2 also discloses to use, as a liquid for use in the hydrolysis of the first step, part of water that is recovered after washing a residue obtained by solid-liquid separation after end of the first step with water, together with the filtrate obtained by solid-liquid separation after end of the second step, and to use the remainder of the slurry in the second step.

On the other hand, a method of continuously separating and washing a solid in a suspension by using a plurality of thickeners is known. Patent document 3 discloses a multistage thickener washing method for washing red mud by arranging a plurality of thickeners for washing in series, wherein part of over flow water of at least one thickener for washing is added to a slurry supplied to the thickener. Similarly, Patent document 4 discloses a method of adding a red mud sedimentation auxiliary agent in sedimentation of red mud, wherein in sedimenting red mud from a red mud slurry generated in the Bayer process in a sedimentation step operated under normal pressure and/or under increased pressure, a red mud sedimentation auxiliary agent is preliminarily added and diluted in a circulating clear liquid and/or washing water of the sedimentation step, and introduced into the red mud slurry to be treated. Patent document 4 also discloses washing red mud by using a plurality of thickeners (FIG. 4).

CITATION LIST

Patent Literature

PTL 1: JP 2010-81855 A
PTL 2: JP 2010-253348 A
PTL 3: JP 57-61624 A
PTL 4: JP 5-229816 A

SUMMARY OF INVENTION

Technical Problem

Since C5 saccharides or C6 saccharides are dissolved in water after the slurry of cellulosic biomass is subjected to a hot water treatment, about 10 to 50 percent of C5 saccharides or C6 saccharides generated in the hot water treatment remain in a residue (dehydrated cake) obtained by a dehydration treatment. When the biomass concentration in the cellulosic biomass slurry is increased to improve the hydrolysis efficiency, the amount of C5 saccharides or the amount of C6 saccharides remaining in the residue after the hot water treatment increases, and it can occupy a half or larger of the generation amount in some cases. Therefore, it is desired to recover C5 saccharides or C6 saccharides from the dehydrated cake.

By washing the dehydrated cake, it is possible to recover C5 saccharides or C6 saccharides from the washing water. In an ordinary hydrolysis method, hemicellulose in biomass is subjected to a hot water treatment (first hot water treatment) and hydrolyzed to C5 saccharides, and the residue is subjected to a dehydration treatment, and the dehydrated cake (solid residue) is rendered a slurry again, and cellulose in biomass is hydrolyzed into C6 saccharides by a hot water treatment (second hot water treatment) under severer conditions. Therefore, it is preferred that the loss of the dehydrated cake due to washing is as small as possible. It is preferred that washing of the dehydrated cake is conducted successively from the view point of the operation efficiency as is the case with the method of using a plurality of thickeners disclosed in Patent document 3 or 4.

If the amount of the washing water is large, the recovery of saccharides increases, and the amount of the saccharified solution also increases, and accordingly the saccharide concentration decreases, and the concentration load in the subsequent concentration step increases.

The lower the water content of the dehydrated cake, the smaller the amount of saccharides dissolved in water, and hence the loss of saccharides can be reduced. However, if the particle size of biomass after saccharification is too large, it is difficult to dehydrate the biomass because its fibrous matter retains water. This results in increase in the water content of the dehydrated cake, and increase in the amount of saccharides remaining in the dehydrated cake.

On the other hand, when a slurry of cellulosic biomass is hydrolyzed in a hot water treatment to give saccharides, it is possible to stop the hydrolysis reaction by flush evaporation, however, it is also important to recover the heat energy of the flush vapor so as to increase the energy efficiency. Here, the finer the cellulosic biomass contained in the slurry, the higher the hydrolysis efficiency, however, the problem of difficulty in solid-liquid separation by a thickener arises. On the contrary, if the cellulosic biomass contained in the slurry is made coarser, the problem that the flush valve is clogged with biomass arises although the power of the grinder required in the grinding step which is a pretreatment is reduced.

In contrast to the method of washing red mud disclosed in Patent document 3 or Patent document 4, in the case of a saccharified solution production method that uses cellulosic biomass as a starting material, scaling occurs in concentrating a saccharified solution by a concentration device such as a reverse osmosis membrane device (RO device), a distillation device or an electro-dialyzer when a suspended matter is contained in a thickener supernatant.

It is an object of the present invention to provide a saccharified solution production method that realizes high saccharide recovery from a dehydrated cake and is less likely to cause scaling in a concentration device at the time of concentrating a saccharified solution, and a saccharified solution production apparatus used for such a saccharified solution production method.

Solution to Problem

The present inventors have made diligent efforts for solving the aforementioned problems, and found that the aforementioned problems can be solved by successively washing a solid in a slurry with washing water by using multiple stages of thickeners for washing that are arranged in series so that the direction of movement of a solid (sediment) in a slurry after a saccharifying step and the direction of movement of overflow water are opposite to each other, and removing a solid residue from recovered washing water by using a thickener for still standing that is different from the thickeners for washing, and finally accomplished the present invention.

Specifically, the present invention relates to a saccharified solution production method that uses cellulosic biomass as a starting material, including:

a saccharifying step of saccharifying hemicellulose or cellulose contained in the cellulosic biomass to C5 saccharides or C6 saccharides by subjecting a slurry of the cellulosic biomass to a hot water treatment in a supercritical state or subcritical state;

a washing step of successively washing a solid in the slurry with washing water after the saccharifying step, by using multiple stages of thickeners for washing arranged in series so that the direction of movement of the solid in the slurry and the direction of movement of overflow water are opposite to each other; and a concentration step of removing a solid residue from the washing water recovered in the washing step by using a thickener for still standing that is different from the thickeners for washing, and then concentrating a supernatant of the thickener for still standing by using a concentration device to give a saccharified solution.

By successively washing a sediment in the slurry with washing water after the saccharifying step, by using multiple stages of thickeners for washing arranged in series so that the direction of movement of the solid (sediment) in the slurry and the direction of movement of overflow water are opposite to each other, it is possible to recover C5 saccharides or C6 saccharides remaining in the solid efficiently into the washing water. Since the washing water has low saccharide concentration as it is, it is concentrated to have a concentration of saccharides of more than or equal to 10% by mass by a concentration device such as a RO membrane device, a distillation device or an electro-dialyzer, and the washing water is introduced to a thickener for still standing that is different from the thickeners for washing, and a suspended matter is removed. Therefore, scaling is less likely to occur in the concentration device.

Preferably, the number of stages of the thickeners for washing is more than or equal to 3 and less than or equal to 6 from the view point of practicality and economy.

Preferably, the saccharified solution production method of the present invention further includes a grinding step of grinding cellulosic biomass to have a mean particle size ranging from 0.1 mm or more and 2 mm or less, before the saccharifying step.

In the washing method disclosed in Patent document 3 or Patent document 4, red mud microparticles of bauxite are washed by a plurality of thickeners arranged in series. However, presumable mean particle size of the red mud microparticles is about 20 μm, and it is difficult to increase the mean particle size from the view point of preventing alumina dissolution. On the other hand, in the saccharified solution production method of the present invention, by grinding cellulosic biomass to have a 50% mean particle size (d50) within a specific range from 100 μm or more and 500 μm or less, and rendering it a slurry, clogging in a flush valve is less likely to occur during flush evaporation, and settling property of the solid in the thickeners is improved. Also it is possible to reduce the water content of the dehydrated cake.

Preferably, the saccharified solution production method of the present invention further includes a flush step of flush evaporating the slurry having experienced the saccharifying step, and flush vapor is recovered in the flush step, and is used for preheating the slurry before the saccharifying step.

The present invention also relates to a saccharified solution production apparatus that uses cellulosic biomass as a starting material including:

a saccharifying device for saccharifying hemicellulose or cellulose contained in the cellulosic biomass to C5 saccharides or C6 saccharides by subjecting a slurry of the cellulosic biomass to a hot water treatment in a supercritical state or subcritical state;

a flush tank for flush evaporating the slurry taken out from the saccharifying device;

a heat recovery means that recovers flush vapor and uses it for preheating the slurry to be fed to the saccharifying device;

multiple stages of thickeners for washing successively arranged in series so that the direction of movement of a solid in the slurry taken out from the flush tank and the direction of movement of overflow water are opposite to each other;

a thickener for still standing for removing a solid residue by leaving the washing water taken out from the thickeners for washing; and a concentration device for concentrating a supernatant of the thickener for still standing.

Advantageous Effects of Invention

The saccharified solution production method and the saccharified solution production apparatus of the present invention achieve high recovery of saccharides, low probability of occurrence of scaling in the concentration device, and high heat efficiency by recovery of heat.

DESCRIPTION OF EMBODIMENTS

Hereinafter, preferred embodiments of the present invention will be explained in reference to the drawings. The present invention is not limited to the following description.

Example 1

(Grinding Step)

Figure 1:
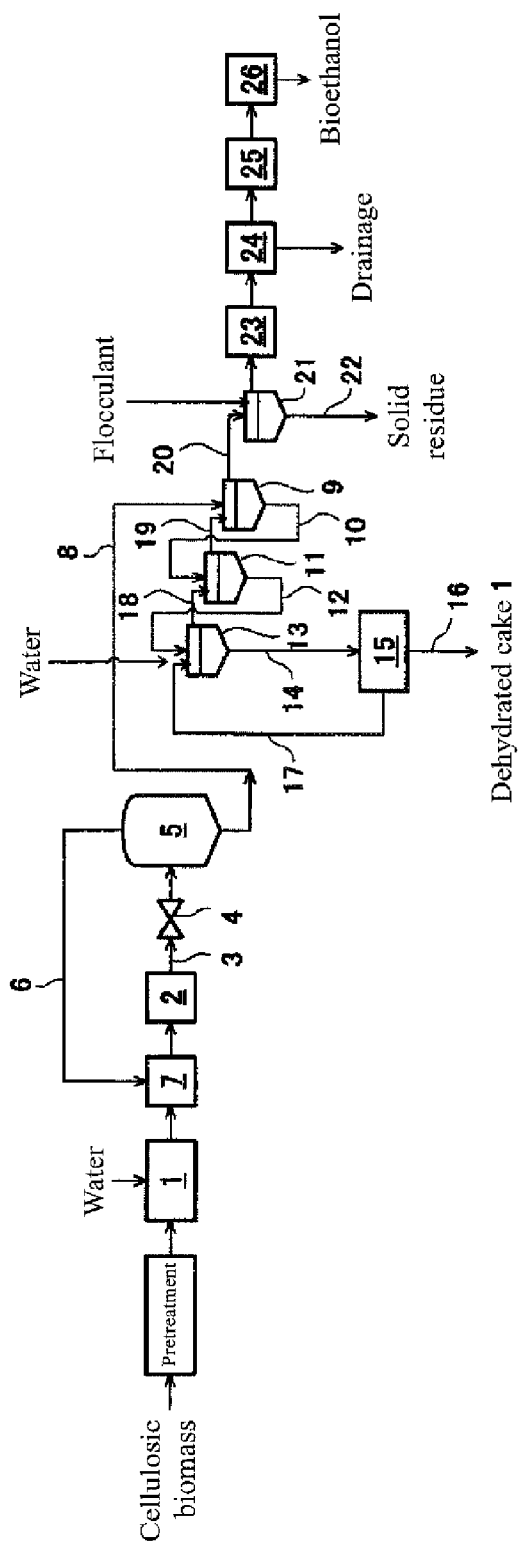
FIG. 1 is a schematic flow chart illustrating a saccharified solution production apparatus of Example 1.

FIG. 1 is a schematic flow chart illustrating a saccharified solution production apparatus of Example 1. First of all, cellulosic biomass (vegetation biomass such as bagasse, beet dregs, or straw) is ground to have a 50% mean particle size in the range of 100 μm or more and 500 μm or less, preferably in the range of 150 μm or more and 400 μm or less by a grinder as a pretreatment. Concrete examples of the grinder include a ball mill, a rod mill, a hammer mill, a cutter mill, a roller mill, a disc mill or a shredder.

The present inventors ground bagasse to have a 50% mean particle size ranging from 100 μm to 1700 μm, and prepared material slurries by using bagasse of different 50% mean particle sizes and subjected them to a hot water treatment. The slurry having experienced the hot water treatment and measuring 50 mL was put in a beaker and water was added so that the total amount was 100 mL, and stirred. Thereafter, suction filtration using filter paper No. 5C was conducted, and the residue on the filter paper was transferred to an evaporating dish, and dried for 12 hours at 107° C. The residue weight before drying and the residue weight after drying were compared to calculate a water content (% by mass). The water content of the residue was less than or equal to 75% when the 50% mean particle size of bagasse falls within the range of 100 μm or more and 500 μm or less, while the water content of the residue exceeded 75% when the 50% mean particle size of bagasse exceeds 600 μm. From the result of this preliminary experiment, it is considered that the cellulosic biomass is preferably ground to have a 50% mean particle size ranging from 100 μm or more and 500 μm or less in the grinding step from the view point of solid-liquid separability of the residue after the saccharification step.

(Preparation of Slurry)

The ground cellulosic biomass is fed to a slurry preparation tank 1, and is stirred after addition of water to give a slurry. Concentration of a solid in the slurry is preferably adjusted to 15 to 40% by mass. The prepared slurry is fed to a saccharifying device 2 (hemicellulose saccharification reactor or cellulose saccharification reactor) via a preheater 7. The preheater 7 is supplied with flush vapor recovered from a flush tank 5 as will be described later, and the slurry to be fed to the saccharifying device 2 is preheated. A concrete example of the saccharifying device 2 is preferably a direct-heating pressure vessel.

(Saccharifying Step)

In the case of saccharifying (hydrolyzing) hemicellulose in the cellulosic biomass to C5 saccharides, the slurry is subjected to a hot water treatment at a temperature ranging from 140° C. or higher and 200° C. or lower, and under a pressure ranging from 1 MPa or higher and 5 MPa or lower in the saccharifying device 2. In the case of saccharifying (hydrolyzing) cellulose in the cellulosic biomass to C6 saccharides, the slurry is subjected to a hot water treatment at a temperature ranging from 240° C. or higher and 300° C. or lower, and under a pressure ranging from 4 MPa or higher and 10 MPa or lower.

(Flush Step)

After conduction of a hot water treatment for a certain time, the slurry is fed to the flush tank 5 from the saccharifying device 2 via a path 3. In the flush tank 5, the slurry is rapidly cooled to a temperature less than or equal to the subcritical state by flush evaporation, and the saccharifying reaction (hydrolysis reaction) ends. The path 3 is provided with a flush valve 4, and movement of the slurry to the flush tank 5 is controlled by the flush valve 4. The flush vapor generated in the flush tank 5 is fed to the preheater 7 via a vapor recovery path 6. On the other hand, the slurry having experienced the hot water treatment is fed to a thickener for washing 9 via a path 8.

In the grinding step, when cellulosic biomass is ground to have a mean particle size ranging from 0.1 mm or more and 2 mm or less, clogging in the flush valve 4 is less likely to occur because the mean particle size of the cellulosic biomass is sufficiently smaller than the width of the slurry path of the flush valve.

(Washing Step)

In the saccharified solution production apparatus illustrated in FIG. 1, three thickeners for washing 9, 11 and 13 are provided in series. The slurry is first fed to the thickener for washing 9, and solid-liquid separated into a solid (sediment) and a supernatant. The solid is taken out from a lower part of the thickener for washing 9, and fed to the thickener for washing 11 via a path 10. The thickener for washing 11 is supplied with overflow water from the thickener for washing 13 via a path 18, and the solid is washed. Overflow water of the thickener for washing 11 is fed to the thickener for washing 9 via a path 19.

The solid washed in the thickener for washing 11 is taken out from a lower part of the thickener for washing 11, and fed to the thickener for washing 13 via a path 12. The thickener for washing 13 is supplied with water, and the solid inside is washed with the water serving as washing water. Overflow water of the thickener for washing 13 is fed to the thickener for washing 11 via the path 18. The solid washed in the thickener for washing 13 is taken out from a lower part of the thickener for washing 13, and fed to a solid-liquid separating device 15 via a path 14. Concrete examples of the solid-liquid separating device 15 include a drum filter, a belt filter, a disc filter, a filter press or a decanter.

A dehydrated cake 1 that is taken out from the solid-liquid separating device 15 via a path 16 may be rendered a slurry again and fed to another saccharifying step, or may be disposed of if not necessary. On the other hand, the water taken out from the solid-liquid separating device 15 is fed to the thickener for washing 13 via a path 17, and reused as washing water.

In the saccharified solution production apparatus illustrated in FIG. 1, the solid in the slurry sequentially moves in the thickeners for washing 9→11→13, and overflow water of the washing water moves in the reverse direction. In other words, the direction of movement of the solid (sediment) in the slurry and the direction of movement of overflow water are opposite to each other. Concentration of C5 saccharides or C6 saccharides is highest in the solid fed to the thickener for washing 9, and concentration of C5 saccharides or C6 saccharides decreases as the solid is fed to the thickeners for washing 11 and 13. On the other hand, regarding the supernatant in the thickener for washing, concentration of C5 saccharides or C6 saccharides is highest in the thickener for washing 13, and concentration of C5 saccharides or C6 saccharide increases as the supernatant is fed as overflow water to the thickeners for washing 13→11→9 because C5 saccharides or C6 saccharides that are eluted from the solid are added. Accordingly, it is possible to recover C5 saccharides or C6 saccharides from the solid efficiently and successively.

While the saccharified solution production apparatus of Example 1 has three thickeners for washing, it is only required that the direction of movement of the solid (sediment) in the slurry and the direction of movement of overflow water are set opposite to each other similarly to Example 1 in the case where four to six thickeners for washing are provided.

(Concentration Step)

Overflow water of the thickener for washing 9 is fed to a thickener for still standing 21 via a path 20. In the thickener for still standing 21, by leaving the overflow water of the thickener for washing 9 still, a fine solid (suspended matter) is removed as a solid residue. The sedimented solid residue is appropriately drained from a path 22. On the other hand, a supernatant of the thickener for still standing 21 is fed to a filter device 23. The filter device 23 is an optional constituent provided for preventing clogging of a RO membrane of a subsequent RO membrane device (concentration device) 24, and may be substituted by other suspended matter removing means, or may be omitted if not necessary.

While a RO membrane device is used as the concentration device in this context, a distillation device or an electro-dialyzer may be used. This also applies to later-described Example 2, Comparative Example 1 and Comparative Example 2.

Treated water of the treatment filter device 23 is fed to the RO membrane device 24. The treated water of the filter device 23 is concentrated by the RO membrane device 24 to have a concentration of saccharides of more than or equal to 10% by mass, and fed to a fermentation tank 25 as a saccharified solution.

To the thickener for washing 9 and/or the thickener for still standing 21, either one or a combination of two or more of a cationic flocculant, an anionic flocculant, a nonionic flocculant and an amphoteric flocculant may be added as necessary. This makes it possible to remove a suspended matter contained in the washing water more effectively. While a flocculant is added to the thickener for still standing 21 in FIG. 1, a flocculant may be added to the thickener for washing 9, and a flocculant may be added to both of the thickener for washing 9 and the thickener for still standing 21.

(Fermentation Step)

The saccharified solution in the fermentation tank 25 is converted to ethanol by utilizing yeast. In the fermentation step, a known alcohol fermentation method can be employed. Through the fermentation step, C5 saccharides or C6 saccharides contained in the saccharified solution are converted to ethanol.

(Distillation Step)

After end of the fermentation step, a fermented solution in the fermentation tank 25 is fed to a distillation device 26 and distilled, and thus ethanol is concentrated. In the distillate obtained in the distillation step, ingredients other than a solid and ethanol have been removed. In the distillation step, a known distillation step that is known as a production method of distilled liquor can be employed.

Example 2

Figure 2:
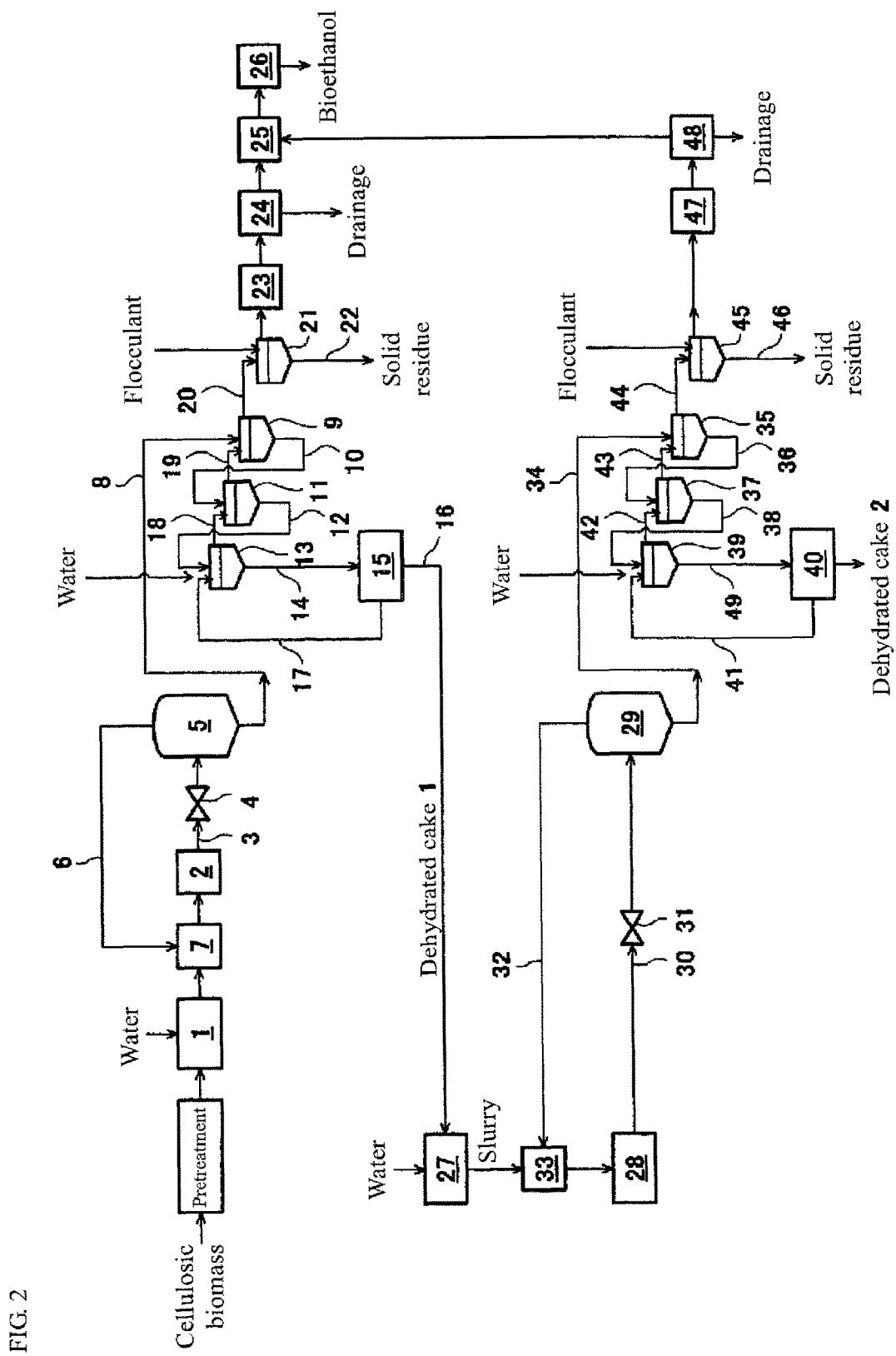
FIG. 2 is a schematic flow chart illustrating a saccharified solution production apparatus of Example 2.

FIG. 2 is a schematic flow chart illustrating a saccharified solution production apparatus of Example 2. Since the fundamental flow of Example 2 is identical to that of Example 1, only differences from Example 1 will be described herein. The same term is used for the same constituent as that of Example 1. In Example 2, after saccharifying (hydrolyzing) hemicellulose in the cellulosic biomass to C5 saccharides, cellulose in the cellulosic biomass is saccharified to C6 saccharides.

(Second Preparation of Slurry)

The slurry of cellulosic biomass is subjected to a hot water treatment at temperature ranging from 140° C. or higher and 200° C. or less, under a pressure ranging from 1 MPa or more and 5 MPa or lower in the saccharifying device 2 (hemicellulose saccharification reactor). Then the dehydrated cake 1 taken out from the solid-liquid separating device 15 through the flush step and the washing step is fed to a slurry preparation tank 27, and stirred with water added thereto, and is rendered a slurry again. Concentration of a solid in the slurry is preferably adjusted to 15 to 40% by mass. The prepared slurry is fed to the saccharifying device 28 (cellulose saccharification reactor) via a preheater 33. The preheater 33 is supplied with flush vapor recovered from a flush tank 29 as will be described later, and the slurry to be fed to the saccharifying device 28 is preheated. A concrete example of the saccharifying device 28 is preferably a direct-heating pressure vessel.

(Second Saccharifying Step)

In the saccharifying device 28, the slurry is subjected to a hot water treatment at a temperature ranging from 240° C. or higher and 300° C. or lower, under a pressure ranging from 4 MPa or higher and 10 MPa or lower in the saccharifying device 2, and thus cellulose in the cellulosic biomass is saccharified to C6 saccharides.

(Second Flush Step)

After conduction of a hot water treatment for a certain time, the slurry is fed to the flush tank 29 through a path 30 from the saccharifying device 28. The slurry is rapidly cooled to a temperature less than or equal to the subcritical state by flush evaporation, and the saccharifying reaction (hydrolysis reaction) of cellulose ends. The path 30 is provided with a flush valve 31, and movement of the slurry to the flush tank 29 is controlled by the flush valve 31. The flush vapor generated in the flush tank 29 is fed to the preheater 33 via a vapor recovery path 32. On the other hand, the slurry having experienced the hot water treatment is fed to a thickener for washing 35 via a path 34.

(Second Washing Step)

In the saccharified solution production apparatus illustrated in FIG. 2, three thickeners for washing 35, 37 and 39 are provided in series for washing a solid in the slurry taken out from the flush tank 29. The slurry is first fed to the thickener for washing 35, and solid-liquid separated into a solid (sediment) and a supernatant. The solid is taken out from a lower part of the thickener for washing 35, and is fed to the thickener for washing 37 via a path 36. The thickener for washing 37 is supplied with overflow water from the thickener for washing 39 via a path 42, and the solid is washed. Overflow water of the thickener for washing 37 is supplied to the thickener for washing 35 via a path 43.

The solid washed in the thickener for washing 37 is taken out from a lower part of the thickener for washing 37, and fed to the thickener for washing 39 via a path 38. The thickener for washing 39 is supplied with water, and the solid inside is washed with the water serving as washing water. Overflow water of the thickener for washing 39 is fed to the thickener for washing 37 via the path 42. The solid washed in the thickener for washing 39 is taken out from a lower part of the thickener for washing 39, and fed to a solid-liquid separating device 40 via a path 49. Concrete examples of the solid-liquid separating device 40 are identical to those of the solid-liquid separating device 15.

A dehydrated cake 2 that is taken out from the solid-liquid separating device 40 is appropriately disposed of. On the other hand, the water taken out from the solid-liquid separating device 40 is fed to the thickener for washing 39 via a path 41, and reused as washing water.

The solid in the slurry sequentially moves in the thickeners for washing 35→37→39, and overflow water of the washing water moves in the reverse direction.

(Second Concentration Step)

Overflow water of the thickener for washing 35 is fed to a thickener for still standing 45 via a path 44. To the thickener for still standing 45, either one or a combination of two or more of a cationic flocculant, an anionic flocculant, a nonionic flocculant and an amphoteric flocculant is added, and a fine suspended matter in the overflow water is removed as a solid residue. The sedimented solid residue is appropriately drained from a path 46. On the other hand, a supernatant of the thickener for still standing 45 is fed to a filter device 47 where a finer suspended matter that cannot be removed by the flocculant is removed.

Treated water of the treatment filter device 47 is fed to a RO membrane device (concentration device) 48. The treated water of the filter device 47 is concentrated by the RO membrane device 48 to have a concentration of saccharides of more than or equal to 10% by mass, and fed to the fermentation tank 25 as a saccharified solution. The treated water of the filter device 47 may be mixed with the treated water of the filter device 23, and may be concentrated by one RO membrane device.

Comparative Example 1

Figure 3:
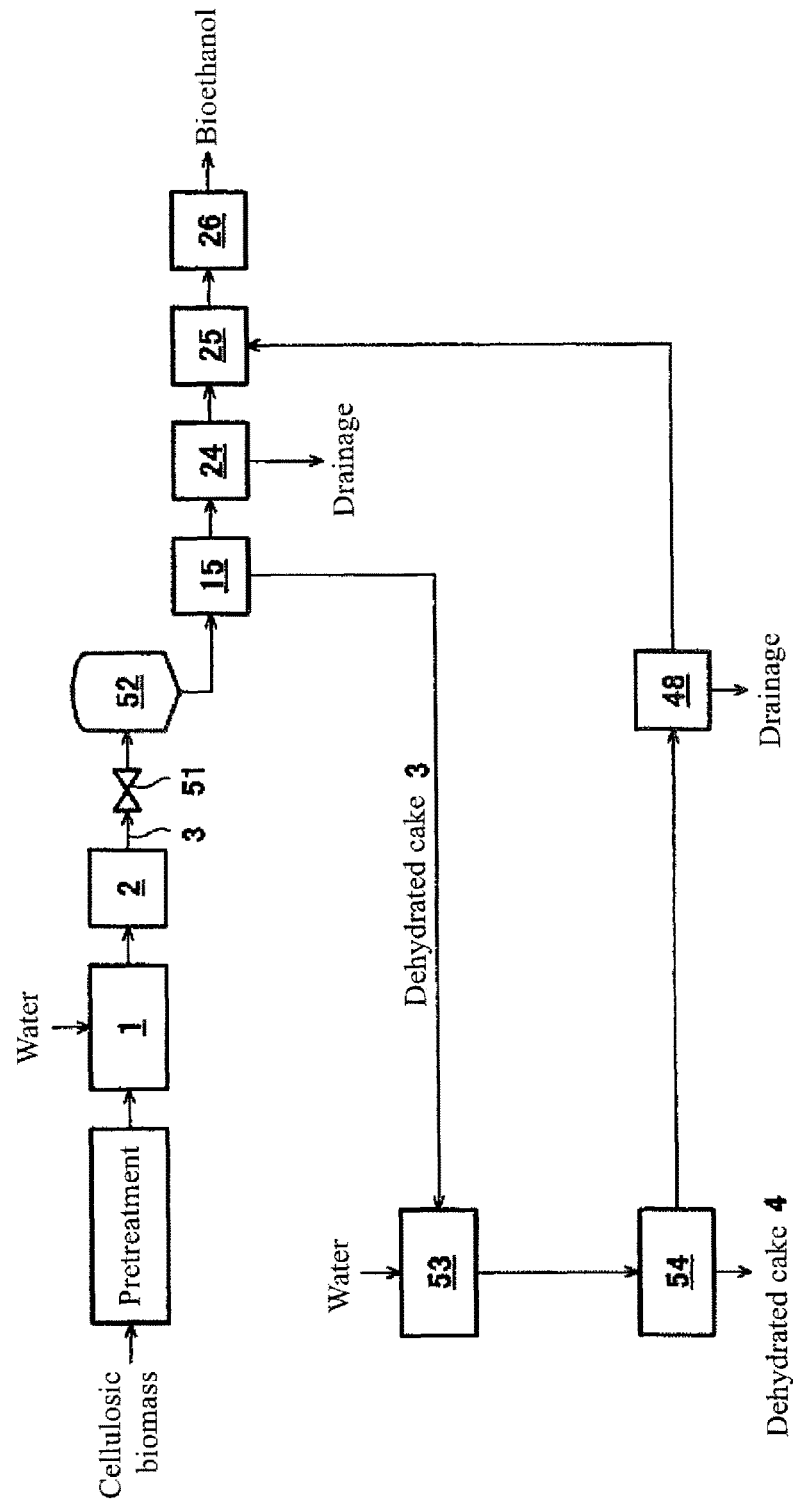
FIG. 3 is a schematic flow chart illustrating a saccharified solution production apparatus of Comparative Example 1.

FIG. 3 is a schematic flow chart illustrating a saccharified solution production apparatus of Comparative Example 1. The same term is used for the same constituent as that of Example 1 and Example 2.

In the saccharified solution production apparatus of Comparative Example 1, after conduction of a hot water treatment for a certain time, the slurry is fed to an indirect cooler 52 from the saccharifying device 2 via the path 3. The path 3 is provided with a drain valve 51, and movement of the slurry to the indirect cooler 52 is controlled by the drain valve 51. Since the slurry is not flush-evaporated unlike the case of the saccharified solution production apparatus of Example 1, it is difficult to rapidly cool the slurry, and C5 saccharides or C6 saccharides generated herein are easy to be excessively decomposed.

After the temperature has fallen, the slurry is fed to the solid-liquid separating device 15 from the indirect cooler 52. The saccharified solution is fed to the RO membrane device (concentration device) 24 and concentrated, and then fed to the fermentation tank 25. On the other hand, a dehydrated cake 3 (solid) taken out from the solid-liquid separating device 15 is fed to a tank 53, and stirred with water added thereto, and is rendered a slurry again. Through this operation, the dehydrated cake 3 is washed, and the remaining C5 saccharides or C6 saccharides are eluted into the washing water.

The prepared slurry is fed to a solid-liquid separating device 54, and solid-liquid separated into washing water and a dehydrated cake 4. The washing water is fed to the RO membrane device (concentration device) 48 and concentrated, and then fed to the fermentation tank 25.

In the saccharified solution production apparatus of Comparative Example 1, the dehydrated cake 3 and water are mixed to recover C5 saccharides or C6 saccharides, and the washing water is recovered by the solid-liquid separating device. In this method, however, concentration of C5 saccharides or C6 saccharides decreases, and the concentration rate required in the concentration device of the subsequent stage increases. This disadvantageously increases the burden of the concentration step.

Comparative Example 2

Figure 4:
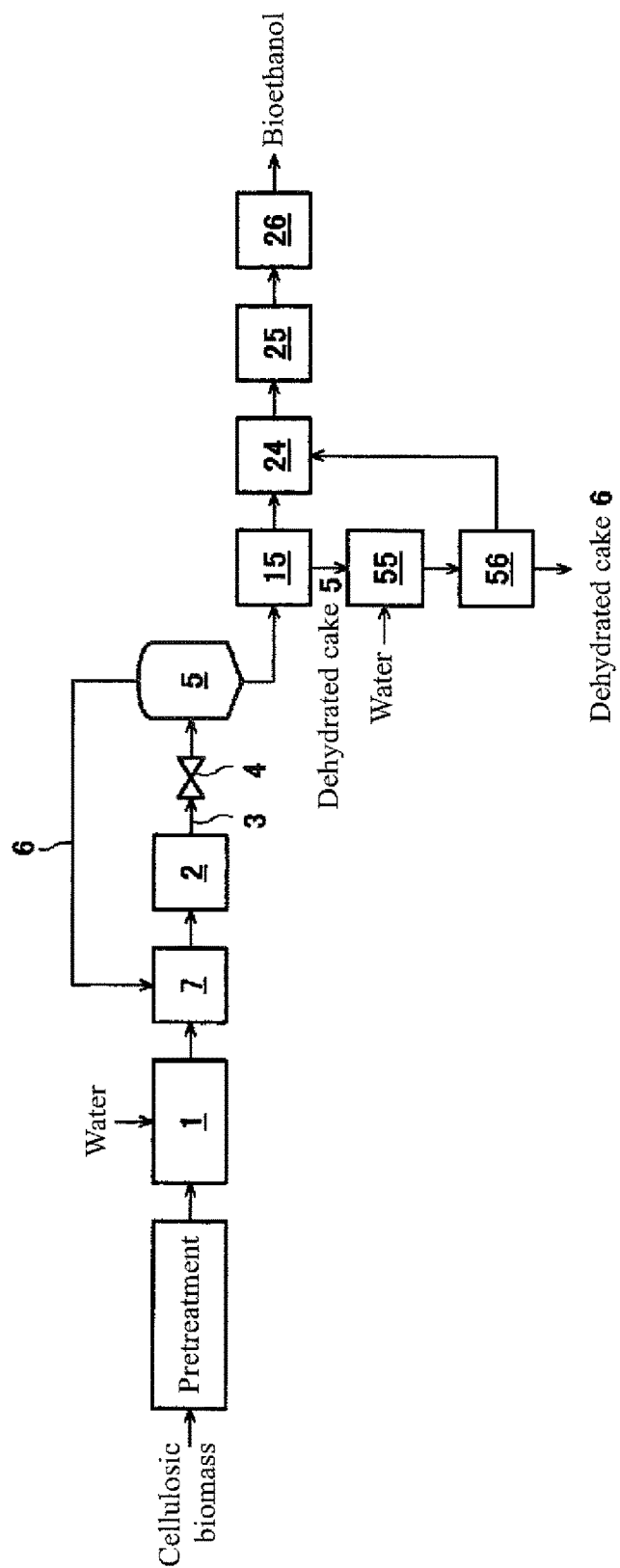
FIG. 4 is a schematic flow chart illustrating a saccharified solution production apparatus of Comparative Example 2.

FIG. 4 is a schematic flow chart illustrating a saccharified solution production apparatus of Comparative Example 2. The same term is used for the same constituent as that of Example 1.

In the saccharified solution production apparatus of Comparative Example 2, the slurry taken out from the flush tank 5 is fed to the solid-liquid separating device 15. The water content (saccharified solution) taken out from the solid-liquid separating device 15 is fed to the RO membrane device (concentration device) 24. On the other hand, a dehydrated cake 5 taken out from the solid-liquid separating device 15 is fed to a tank 55, and stirred with water added thereto, and is rendered a slurry again.

The slurry is fed to a solid-liquid separating device 56. A water content (washing water) taken out from the solid-liquid separating device 56 is fed to the RO membrane device 24. The concentrated saccharified solution is fed to the fermentation tank 25. On the other hand, a dehydrated cake 6 taken out from the solid-liquid separating device 56 may be rendered a slurry again and fed to another saccharifying step, or may be disposed of if not necessary Also in the saccharified solution production apparatus of Comparative Example 2, the dehydrated cake 5 and water are mixed to recover saccharides C5 or C6 saccharides, and the washing water is recovered by the solid-liquid separating device. This method disadvantageously requires an increased number of solid-liquid separating devices.

INDUSTRIAL APPLICABILITY

The saccharified solution production method and the saccharified solution production apparatus of the present invention are useful in bioenergy fields as a production method and a production apparatus for decomposing cellulosic biomass to produce a saccharified solution.

REFERENCE SIGNS LIST 1, 27 slurry preparation tank
2, 28 saccharifying device
3, 8, 10, 12, 14, 16, 17, 18, 19, 20, 22 path
4, 31 flush valve
5, 29 flush tank
6, 32 vapor recovery path
7, 33 preheater
9, 11, 13 thickener for washing
15, 40, 54, 56 solid-liquid separating device
21, 45 thickener for still standing
23, 47 filter device
24, 48 reverse osmosis membrane device (concentration device)
25 fermentation tank
26 distillation device
30, 34, 36, 38, 41, 42, 43, 44, 46, 49 path
35, 37, 39 thickener for washing
51 drain valve
52 indirect cooler
53, 55 tank

The invention claimed is:

1. A saccharified solution production method that uses cellulosic biomass as a starting material having all the limitations claimed as whole, comprising:
   a saccharifying step of saccharifying hemicellulose or cellulose contained in the cellulosic biomass to C5 saccharides or C6 saccharides by subjecting a slurry of the cellulosic biomass to a hot water treatment in a supercritical state or subcritical state;
   a washing step of successively washing a solid in the slurry with washing water after the saccharifying step, by using multiple stages of thickeners for washing arranged in series so that the direction of movement of the solid in the slurry and the direction of movement of an overflow washing water are opposite to each other; and
   a concentration step of removing a solid residue from overflow washing water recovered in the washing step by using a thickener that is different from the thickeners for washing, and then concentrating a supernatant of the different thickener by using a concentration device to give a saccharified solution.

2. The saccharified solution production method according to claim 1, wherein the number of stages of the thickeners for washing is more than or equal to 3 and less than or equal to 6.

3. The saccharified solution production method according to claim 1, further comprising:
   a grinding step of grinding the cellulosic biomass to have a 50% mean particle size ranging from 100 μm or more and 500 μm or less, before the saccharifying step.

4. The saccharified solution production method according to claim 1, further comprising:
   a flush step of flush evaporating the slurry after the saccharifying step,
   wherein flush vapor is recovered in the flush step, and is used for preheating the slurry before the saccharifying step.

5. A saccharified solution production apparatus that uses cellulosic biomass as a starting material apparatus as having all the limitations claimed as whole, comprising:
   a saccharifying device for saccharifying hemicellulose or cellulose contained in the cellulosic biomass to C5 saccharides or C6 saccharides by subjecting a slurry of the cellulosic biomass to a hot water treatment in a supercritical state or subcritical state;
   a flush tank for flush evaporating slurry taken from the saccharifying device;
   a heat recovery means that recovers flush vapor and uses it for preheating slurry to be fed to the saccharifying device;
   multiple stages of thickeners for washing successively arranged in series so that the direction of movement of a solid in slurry taken from the flush tank and the direction of movement of an overflow washing water are opposite to each other;
   a thickener for removing a solid residue from overflow washing water taken from the thickeners for washing; and
   a concentration device for concentrating a supernatant of the thickener for removing a solid residue from the overflow washing water taken from the thickeners for washing.

* * * * *